US005318912A

United States Patent [19]
Silver et al.

[11] Patent Number: 5,318,912
[45] Date of Patent: Jun. 7, 1994

[54] GAS SENSORS AND COMPOUNDS SUITABLE THEREFOR

[75] Inventors: Jack Silver, London; Kenneth R. Rickwood, Colchester; Mustafa T. Ahmet, Beckenham, all of England

[73] Assignee: British Technology Group Limited, London, England

[21] Appl. No.: 862,546

[22] PCT Filed: Nov. 7, 1990

[86] PCT No.: PCT/GB90/01707

§ 371 Date: Jun. 23, 1992

§ 102(e) Date: Jun. 23, 1992

[87] PCT Pub. No.: WO91/07659

PCT Pub. Date: May 30, 1991

[30] Foreign Application Priority Data

Nov. 8, 1989 [GB] United Kingdom ............... 8925246
Nov. 8, 1989 [GB] United Kingdom ............... 8925247
Jan. 24, 1990 [GB] United Kingdom ............... 9001634
Jan. 24, 1990 [GB] United Kingdom ............... 9001637

[51] Int. Cl.$^5$ ............... G01N 21/25; G01N 27/12
[52] U.S. Cl. ............... 436/151; 422/88; 436/124; 436/166
[58] Field of Search ............... 422/57, 61, 88, 90, 422/98; 436/124, 151, 166; 540/121

[56] References Cited

U.S. PATENT DOCUMENTS 5,135,717 8/1992 Renzoni et al. ............... 422/61

FOREIGN PATENT DOCUMENTS 2383440 10/1978 France .
2111987A 7/1983 United Kingdom .
2186087A 8/1987 United Kingdom .

OTHER PUBLICATIONS

Honeybourne et al "Use of Thin Films of Conjugated . . ." J. Chem. Soc. Faraday Trans. 1, (1984), 80, pp. 851–863.

Honeybourne et al "Thin Films of Conjugated . . ." Sensors & Actuators, vol. 15, No. 4 (1988), pp. 359–373.

Primary Examiner—Jill A. Johnston
Attorney, Agent, or Firm—Nixon & Vanderhye

[57] ABSTRACT

A gas sensor has a gas-sensing component which changes color and/or conductivity on exposure to certain gases, which component comprises a (mono, di or tri) azatetrabenzoporphyrin. Certain (mono, di or tri) azatetrabenzoporphyrins containing a transition metal ion selected from chromium (III), vanadyl, manganese, cobalt or iron (III) are novel.

3 Claims, 4 Drawing Sheets

GAS SENSORS AND COMPOUNDS SUITABLE THEREFOR

This invention relates to gas sensors and to certain novel compounds which are suitable for use in gas sensors.

The ability of phthalocyanines, and certain other semiconducting complex ring systems, to act as gas sensing materials has been known for some years. Thus GB-A-2111987 and GB-A-2186087 disclose the use of multi-ring organic semi-conducting compounds in the detection of "NOX" gases. The use of organometallic derivatives of phthalocyanine, meso-tetraarylporphin and dihydrodibenzotetraazaannulene to detect chlorine and NOX gases is also discussed in J. Chem. Socl, Faraday Trans. 1, 80, No. 4, 1984, 851–863, J. Phys. Chem. Solids, 49, No. 9, 1988, 1003–1008 and Sensors and Actuators, 15, No. 4, 1988, 359–370, while FR-A-2383440 discloses the use of symmetrical phthalocyanine and porphyrin organometallics in the detection of a range of gases. Gas detection is effected by virtue of changes in conductivity and/or spectral properties of the semi-conductors.

There is a need to develop further improved methods of detecting the presence of gases, for example the presence, and preferably also the concentration, of industrial pollutant gases in order to distinguish therebetween. The present invention therefore seeks to provide gas sensors exhibiting improved sensitivity and selectivity.

According to the present invention a gas sensor comprises as the gas-sensing component, which changes colour and/or electrical conductivity on exposure to certain gases, a (mono, di or tri) azatetrabenzoporphyrin. The benzoporphyrin may optionally contain a metal. Mixtures of the macrocycles may be employed. A bank of such sensors may be provided, of graded sensitivity, to reveal (by how many in the bank were affected) the concentration of any temporary exposure to gas.

We have surprisingly found that, while it is known that phthalocyanine is easier to oxidise than is prophyrin, the mono-, di- or triazatetrabenzoporphyrins of the invention are even easier than either phthalocyanine or porphyrin. The oxidation potentials of these various compounds are different, and this can be exploited by using a specific compound of appropriate oxidation potential to respond selectively to desired gases. In furtherance of such selectivity, the compound may be appropriately substituted.

An oxidant/reductant sensor according to the invention, which can sense dissolved gases such as chlorine, nitrogen oxides, $SO_2$, $H_2S$ and bromine in water and also ions resulting therefrom and other ions which may be present such as perchlorate and dithionite, comprises a tetrabenzoazaporphyrin as set forth above, which tetrabenzoazaporphyrin covers an area of a support which is stationed in or which is capable of being moved into and out of a location in which it is exposed to the oxidant/reductant. The sensors may be passive or active. Thus passive sensors (such as badges or coated dipsticks) will show a colour change on exposure to a gas or a solution of oxidant or reductant (such as a chlorine-contaminated water reservoir) which change can be monitored by subsequent measurement of optical absorption change. Alternatively, means may be provided to apply a potential difference across the macrocycle component and measure the current required to restore the original colour as a measure of the oxidant/reductant content of the environment. Active sensors may monitor a change in either or both of optical absorption and electrical conduction in an on going manner.

The tetrabenzoazaporphyrin preferably contains at least one metal. Suitably, the metal is in the form of a transition metal ion, optionally associated with an anion or anionic ligand.

Certain triazatetrabenzoporphyrins have previously been prepared. Thus J. Chem. Soc., 1938, 1–6 discloses the preparation of copper tetrabenzotriazaporphyrin as a pigment. Copper, zinc, magnesium and iron (II) tetrabenzotriazaporphyrins were investigated by Barrett, Linstead and Tuey, J. Chem. Soc., 1939, 1809–1820. The properties of highly conducting molecular crystals of (triazatetrabenzoporphyrinato) copper (II) iodide were investigated by Liou et al., Inorg. Chem., 1989, 28, 3889–3896. However, none of these workers recognized the ability of the mono-, di- and triazatetrabenzoporphyrins to act as gas sensors. Furthermore, we have prepared certain novel tetrabenzoazaporphyrins which may be employed as gas sensors as described above and/or which may also find use as electrochromic materials.

Thus according to a further aspect of the present invention we provide a (mono, di or tri) azatetrabenzoporphyrin or a mixture thereof containing a transition metal ion, optionally associated with an anion or an anionic ligand, the transition metal ion being selected from vanadyl, chromium(III), iron(III), manganese or cobalt. The optional anion or ligand may be, for example, oxide, chloride or bromide.

The gas sensor of the invention may, if desired, be provided with means to vary the temperature of the gas sensing component. Furthermore, if desired in order to increase reproducibility, the gas-sensing component may be pre-treated, for example by preheating prior to exposure to the gas. The gas-sensing component may be exposed to the gas to be detected in gaseous state or in solution, preferably aqueous solution.

The tetrabenzoazaporphyrins may conveniently be prepared by condensation of dicyanobenzene with an appropriate Grignard reagent, for example methyl magnesium iodide, followed by introduction of the desired transition metal ion by reaction with an appropriate metal salt, such as chromium chloride. The gas sensing components are preferably employed deposited on suitable plates or slides, preferably by sublimation, but alternatively by other techniques for obtaining a thin layer such as Langmuir-Blodgett multiple molecular layer deposition or by evaporation.

The invention will now be further described by way of example.

EXAMPLE 1

Synthesis of chromium tetrabenzotriazaporphyrin (1)

5 g (0.04 moles) of dicyanobenzene were placed in 250 ml diethyl ether. With stirring, an equimolar amount of $CH_3MgI$ was added. Immediately after, 2.66 g (0.01 moles) of chromium chloride hexahydrate was added.

There was an immediate vigorous reaction with the mixture turning red/brown. The mixture was heated and allowed to reflux for 1 hour and then the ether was boiled off.

The resultant brown powder was heated in an oven to 330° C., then water was added dropwise. When the emission of iodine vapour had stopped, the solid was heated for a further half hour.

After cooling the now blue/black solid was washed with 10% HCl containing absolute alcohol and then with hot ammonia solution. The final product was dried in an oven at 100° C. and purification was achieved by sublimation.

The material was identified by its ultraviolet and visible spectra in the solid phase and exhibited a major peak at 697 nm, a shoulder at 630 nm and a minor peak at 490 nm.

EXAMPLE 2

Synthesis of Fe(III)Tetrabenzoazaporphyrins

Iron mono-, di- and tri-azatetrabenzoporphyrin were in each case made by reacting phthalonitrile with a Grignard reagent. The composition of the Grignard was varied dependent on the compound to be formed as follows:

| Azotetrabenzoporphyrin | Grignard | |
|---|---|---|
| mono- | Mg powder | 3.6 g |
|  | iodomethane | 9.75 ml |
|  | diethyl ether | 150 ml. |
| di- | Mg powder | 2.4 g |
|  | iodomethane | 6.5 ml |
|  | diethyl ether | 150 ml. |
| tri- | Mg powder | 1.2 g |
|  | iodomethane | 3.25 ml |
|  | diethyl ether | 150 ml. |

The Grignard reagent in each case was prepared by the addition of magnesium powder and iodomethane to diethyl ether. A small crystal of iodine was added to assist the reaction. The mixture was continuously stirred and the reaction effervesced followed by deposition of magnesium hydroxide on completion.

The Grignard reagent (of the appropriate composition as described above for each azatetrabenzoporphyrin) was decanted onto phthalonitrile (6.4 g) and stirred (30 minutes). Red/brown mixtures were obtained which got progressively lighter in going from the mono- to di- to triaza compound. Ether was evaporated and ammonium chloride added to the resulting solids. The reactions were exothermic and produced brown mixtures which, when filtered, yielded brown solids which got progressively lighter from mono- to di- to triaza compounds. The macrocycles were refluxed with anhydrous ferric chloride (2.03 g) in chloronaphthalene to give green solutions with blue/black residues which were identified spectroscopically. The chloro derivatives so formed were refluxed in pyridine to see if any change occurred in the electronic environment of the iron in the compounds.

The electrochromic properties of the three tetrabenzoazaporphyrins were investigated. The monoaza material (as a sublimed film) showed a colour change from blue (neutral form) to red/purple (reduced form). The diaza material showed a colour change from green (neutral form) to red (reduced form). The triaza material showed a colour change from blue (neutral form) to red (reduced form).

EXAMPLE 3

Synthesis of alternative tetrabenzotriazaporphyrins

The following further materials were prepared by a method analogous to that described in Example 1 but introducing alternative metals to the initially formed tetrabenzotriazaporphyrin.

3. $(VO)^{2+}$ tetrabenzotriazaporphyrin
4. Cr (III) tetrabenzotriazaporphyrin
5. Mn tetrabenzotriazaporphyrin
6. Co tetrabenzotriazaporphyrin

EXAMPLE 4

Detection of chlorine

The materials prepared in Examples 1 and 3, and also copper (II) tetrabenzotriazaporphyrin, prepared by the method described by Barrett, Linstead and Tuey, J. Chem. Soc., 1939, 1809–1820, were tested for chlorine response. Plates were prepared for testing by subliming the gas sensing material onto the back of an indium-tin-oxide coated glass slide provided with contact pads for resistive heating of the oxide if desired. Suitable apparatus is described in International Patent Application No. PCT/GB90/01706, Publication No. WO91/07658.

The results are shown in Table 1 and 2 as ratios of recovery and change. The column headings have the following meanings:

ABS BEFORE is the optical absorption before exposure to the chlorine.

ABS AFTER is the optical absorption immediately after the exposure.

ABS REC 2 is the optical absorption after 2 hours recovery, and

ABS REC 24 likewise after 24 hours recovery. In Table 2, the materials are ranked in descending order of their ability to recover after 24 hours; in a perfect material, ABS REC 24/ABS BEFORE would be 1.00. Some very interesting effects emerge:

1. The Cr material shows very good recovery on heating.
2. The Co material shows good recovery but only at one wavelength out of the two examined. The material was a mixture of two phases. The two wavelengths examined correspond to the peaks of the $\alpha$ and $\beta$ phases respectively. The $\beta$ phase is the phase that showed good recovery. This is a high temperature phase which one formed is fairly stable.
3. The Mn material and the vanadyl material show slight recovery.

In use, the temperature is raised (e.g. to 130° C.) to condition the sensor, although a non-preheat-treated plate allowed to recover overnight after exposure to gas may be as good.

At 190° C., recovery after an experiment can be as quick as 4 minutes.

On a subsequent exposure to gas, the absorption change and recovery are both less (but still amply useful), possibly due to a phase change.

TABLE 1

| | OPTICAL ABSORPTION DATA | | | | |
|---|---|---|---|---|---|
| METAL | λ(nm) | ABS BEFORE | ABS AFTER | ABS REC 2 | ABS REC 24 |
| VO | 680 | 2.20 | .38 | .62 | .70 |
| Cr | 695 | .94 | .22 | .88 | .89 |
| Mn | 678 | 1.14 | .35 | .50 | .54 |
| Co | 618 | 1.36 | .56 | .77 | .80 |
| Co | 680 | 1.19 | .47 | .87 | .97 |

TABLE 1-continued

| | | OPTICAL ABSORPTION DATA | | | |
|---|---|---|---|---|---|
| METAL | λ(nm) | ABS BEFORE | ABS AFTER | ABS REC 2 | ABS REC 24 |
| Cu | 615 | .75 | .38 | .48 | .53 |
| Cu | 675 | .74 | .33 | .43 | .46 |

TABLE 2

| | OPTICAL ABSORPTION DATA | | |
|---|---|---|---|
| METAL | ABS AFTER / ABS BEFORE | ABS REC 2 / ABS BEFORE | ABS REC 24 / ABS BEFORE |
| Cr | .23 | .94 | .95 |
| Co | .39 | .73 | .82 |
| Cu | .51 | .64 | .71 |
| Cu | .45 | .58 | .62 |
| Co | .41 | .57 | .59 |
| Mn | .31 | .44 | .47 |
| VO | .17 | .28 | .32 |

EXAMPLE 5

Gas sensors using chromium tetrabenzotriazaporphyrin

From the foregoing, the most promising compound was identified as chromium tetrabenzotriazaporphyrin, and this was then made up into further gas sensors according to the invention, exploiting the electrical conductivity change which it has been found to exhibit.

A glass slide was prepared coated on one side with indium-tin-oxide and provided with contact pads, whereby the slide could be resistively heated as required. On the other side of the slide, interdigitated gold electrodes of equivalent length 100 mm and interelectrode spacing 0.5 mm were deposited, and then the chromium tetrabenzotriazaporphyrin was sublimed onto that other side of the slide, whereby its conductivity could be measured at any temperature when exposed to any gas. Further details of a conductivity cell which could be used will be found in W091/07658 mentioned above.

Table 3 shows the results of consecutive repetitions of exposure of the slide to chlorine on the current passed at constant voltage of various samples (arbitrarily designated F-J). The % rise in current gives a measure of sensitivity.

TABLE 3

Material: sublimed chromium tetrabenzotriazaporphyrin

| Sample | chlorine concentration ppm | temperature °C. | Initial current μA | current after 2 mins μA | % rise in current |
|---|---|---|---|---|---|
| F | 5 | 130 | 0.3 | 50 | 16500 |
| | 5 | 130 | 2 | 58 | 2800 |
| | 5 | 190 | 25 | 51 | 104 |
| | 5 | 190 | 28 | 73 | 160 |
| | 5 | 130 | | | |
| | 5* | 130 | 23 | 36 | 56 |
| G | 5§ | 130 | 0.1 | 25 | 24900 |
| | 5* | 130 | 50 | 71 | 42 |
| | 5* | 130 | 60 | 74 | 23 |
| | 5* | 130 | 65 | 79 | 21 |
| | 5* | 130 | 74 | 82 | 11 |
| H | 1 | 130 | 14 | 21 | 50 |
| | 1 | 130 | 21 | 47 | 123 |
| | 1 | 130 | 31 | 48 | 54 |
| | 5 | 130 | 14 | 49 | 250 |
| | 5 | 130 | 32 | 60 | 87 |
| | 1 | 130 | 27 | 56 | 107 |
| | 1 | 130 | (33) | 61 | 84 |
| | 1 | 130 | 16 | 38 | 137 |
| | 1 | 130 | 29 | 46 | 58 |
| | 20 | 130 | 48 | 92 | 91 |

TABLE 3-continued

Material: sublimed chromium tetrabenzotriazaporphyrin

| Sample | chlorine concentration ppm | temperature °C. | Initial current μA | current after 2 mins μA | % rise in current |
|---|---|---|---|---|---|
| | 20† | 130 | 45 | 89 | 98 |
| | 1§ | 130 | 0.2 | 13.4 | 6600 |
| | 1 | 130 | 8.9 | 23.5 | 164 |
| | 1 | 130 | 16.4 | 29.9 | 82 |
| | 1 | 130 | 22.5 | 35.5 | 57 |
| | 5 | 130 | 26.4 | 57.2 | 116 |
| J | 5 | 130 | 43.3 | 67.3 | 55 |
| | 5 | 130 | 54.6 | 75.5 | 38 |
| | 5 | 130 | 62.7 | 82.0 | 30 |
| | 20 | 130 | 65.5 | 103.3 | 7 |
| | 20 | 130 | 87.4 | 113.9 | 31 |
| | 20 | 130 | 98 | 120.5 | 22 |
| | 20 | 130 | 106.2 | 126.5 | 19 |

*reduced response due to previous heat treatment in the presence of chlorine
( )estimated values
† one intervening run omitted
§first exposure

EXAMPLE 6

Comparison of gas sensing behavior of phthalocyanines and tetrabenzotriazaporphyrins Given the structural similarity of phthalocyanine and tetrabenzotriazoporphyrin, it was to be expected that their spectral, gas sensing and electrochromic properties would be similar. This was surprisingly found not to be the case and is graphically illustrated with respect to the gas sensing of chlorine gas by examining the resulting optical changes for several tetrabenzotriazaporphyrins, prepared as described above, and the corresponding phthalocyanine compound.

In the study chlorine gas was used in various concentrations ranging from 250 ppm to 100%. Phthalocyanine itself showed no appreciable change in its visible spectrum even at 100% chlorine concentration. By comparison tetrabenzotriazaporphyrin films could detect concentrations of 250 ppm and were oxidised completely and instantly by chlorine concentrations over ca. 10%.

BRIEF DESCRIPTION OF THE FIGURES

The results are shown graphically in FIGS. 1 to 7. In each case the solid line represents the spectrum before exposure to chlorine and the dotted line represents the spectrum after exposure to chlorine (at a concentration of about 10% in ambient air).

Figure 1:
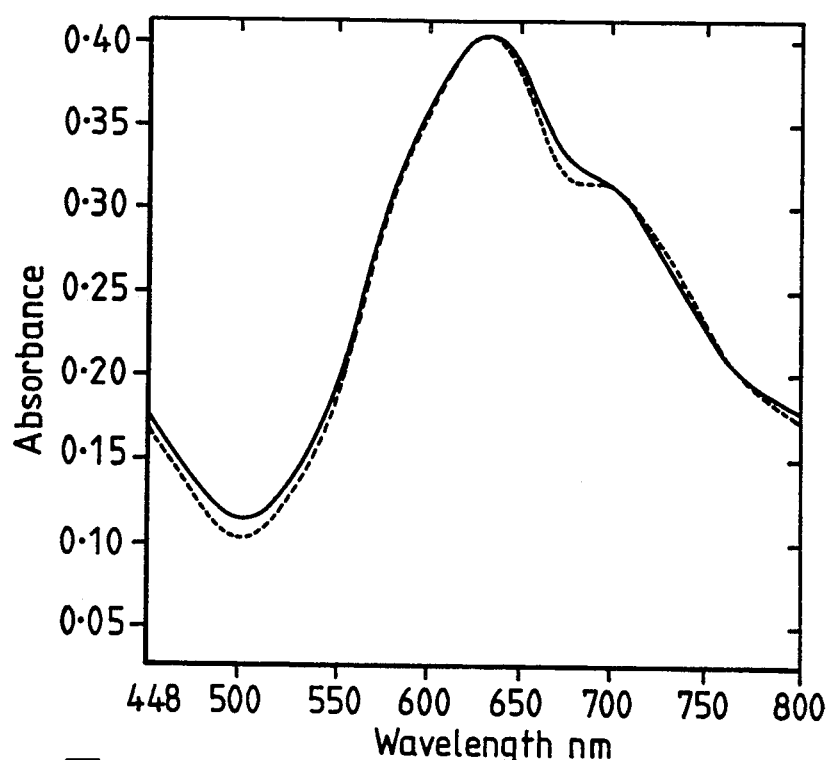
FIG. 1—phthalocyanine
FIG. 2—tetrabenzotriazaporphyrin
FIG. 3—Mn phthalocyanine
FIG. 4—Mn tetrabenzotriazaporphyrin
FIG. 5—vanadyl phthalocyanine
FIG. 6—vanadyl tetrabenzotriazaporphyrin
FIG. 7—chromium (III) tetrabenzotriazaporphyrin
Figure 2:
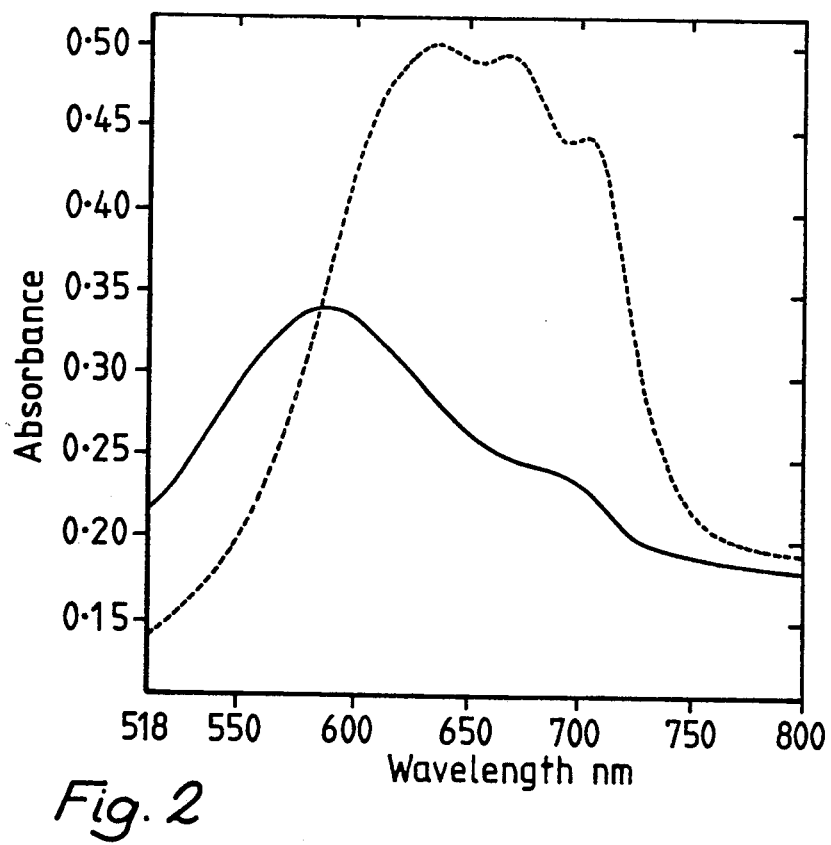
Figure 3:
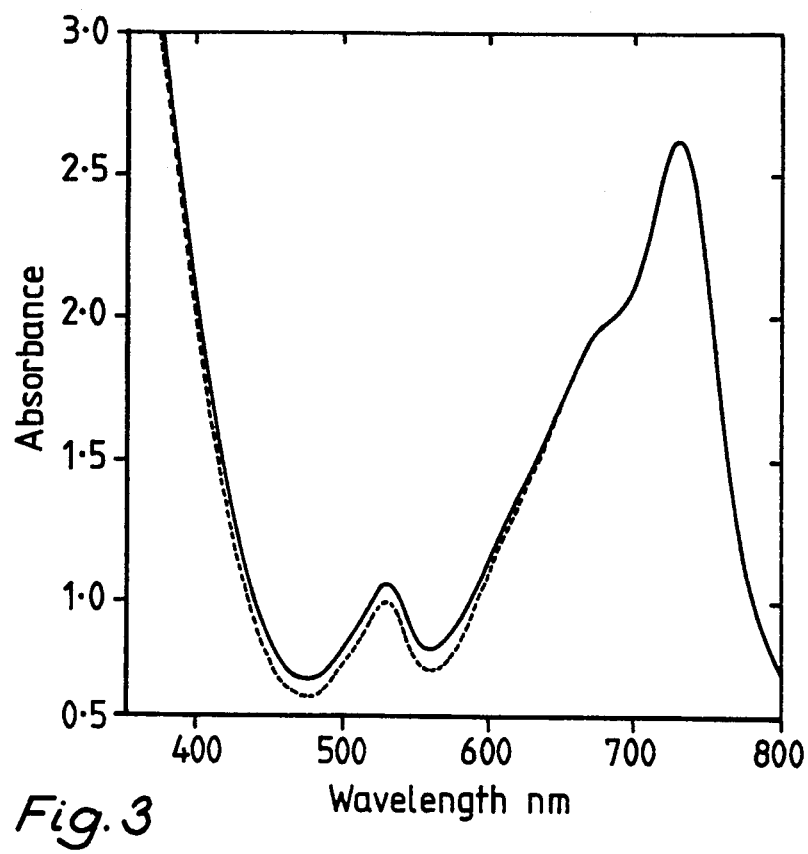
Figure 4:
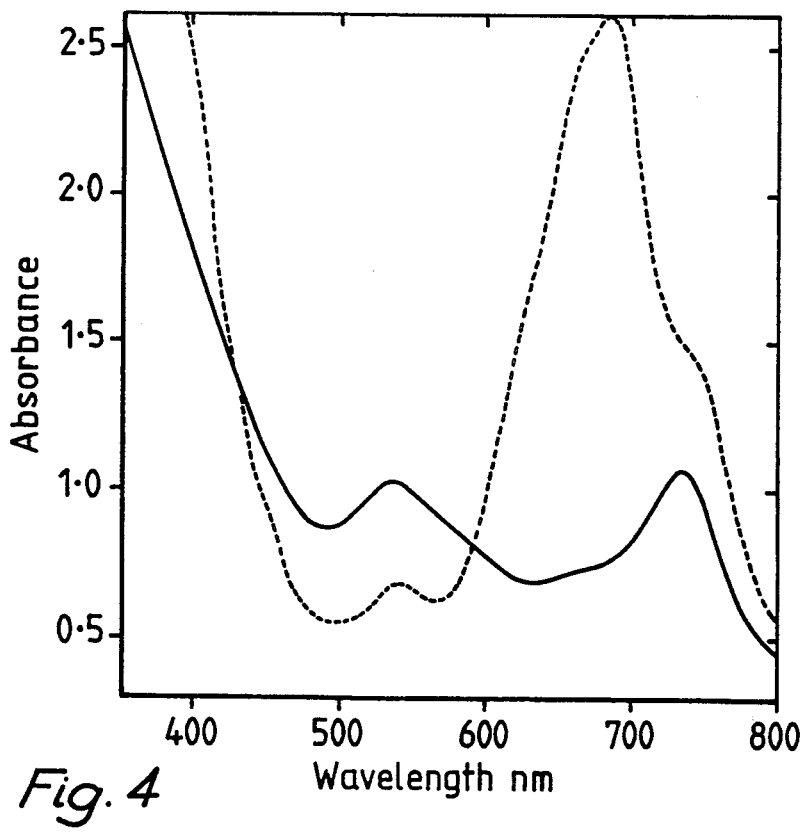
Figure 5:
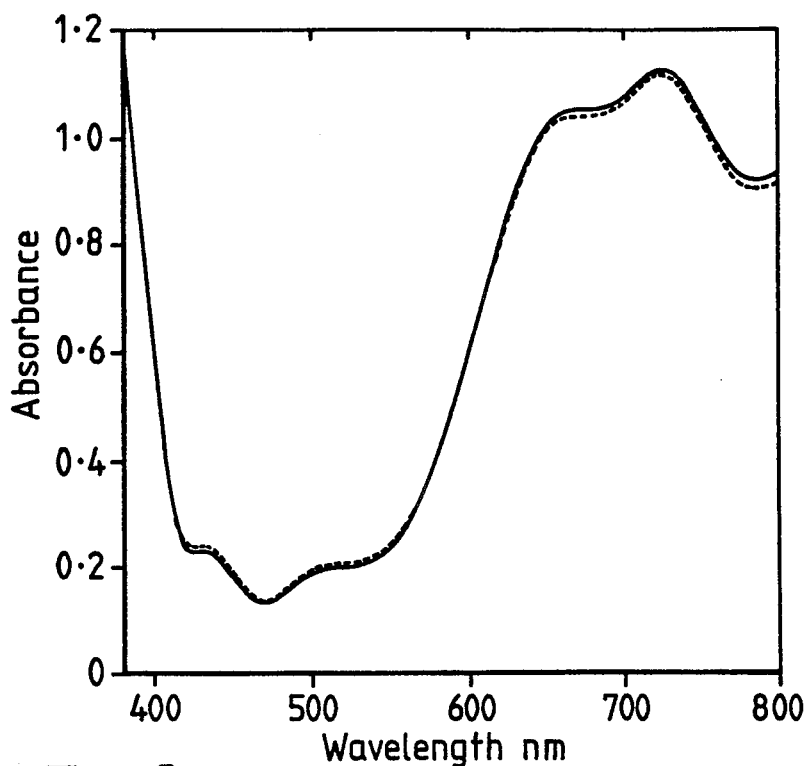
Figure 6:
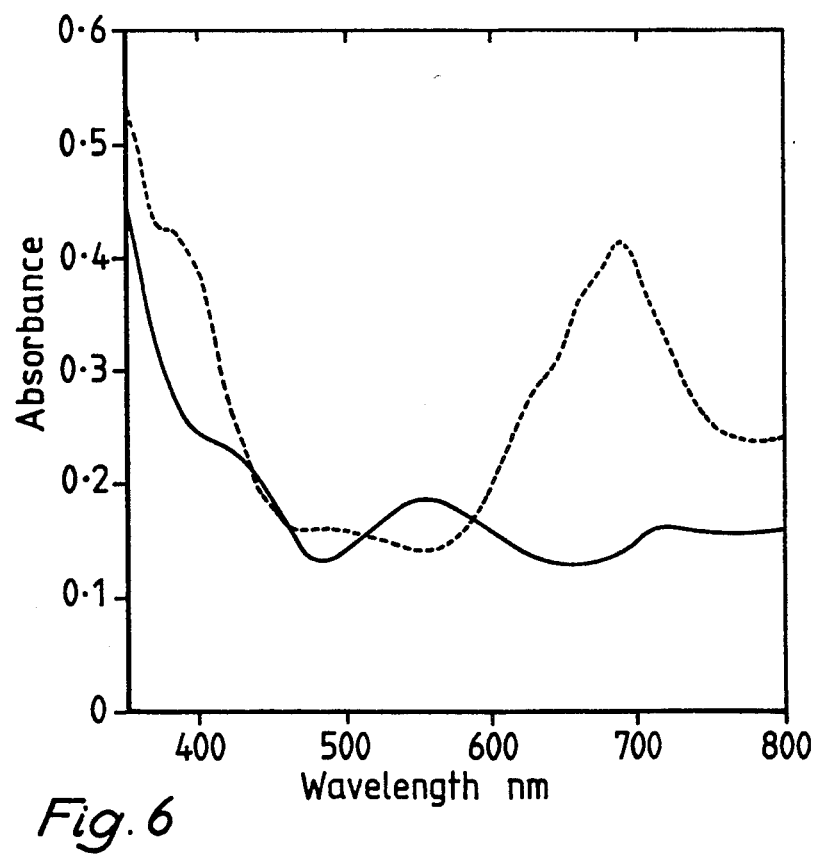
Figure 7:
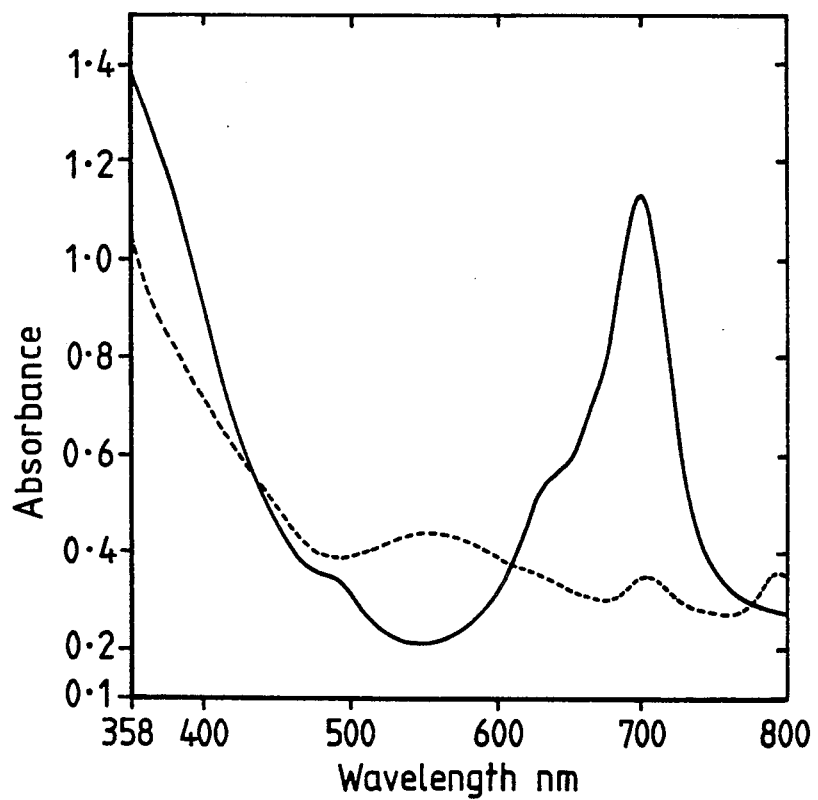

We claim:

1. A method of detecting gases comprising the steps of:
    exposing a gas sensing component to a gas; and
    detecting a color and/or electrical conductivity change in the gas sensing component characteristic of the gas, wherein the gas sensing component comprises a thin layer of a mono-, di- or tri-azatetrabenzoporphyrin containing at least one transition metal ion selected from the group consisting of chromium (III), vanadyl, manganese, cobalt and iron (III).

2. The method according to claim 1, wherein the gas-sensing component comprises a tetrabenzotriazaporphyrin.

3. The method according to claim 1, wherein the gas-sensing component is preheated prior to exposure to the gas.